(12) United States Patent
Haimson et al.

(10) Patent No.: US 11,651,252 B2
(45) Date of Patent: May 16, 2023

(54) PROGNOSTIC SCORE BASED ON HEALTH INFORMATION

(71) Applicant: Flatiron Health, Inc., New York, NY (US)

(72) Inventors: Joshua D. Haimson, Brooklyn, NY (US); Shrujal Baxi, Rye, NY (US); Neal Meropol, Brooklyn, NY (US); Geetu Ambwani, New York, NY (US); Daniel Backenroth, New York, NY (US); Mahesh Murali, New York, NY (US); Andrej Rosic, New York, NY (US); Chengsheng Jiang, Jersey City, NJ (US)

(73) Assignee: Flatiron Health, Inc., New York, NY (US)

( * ) Notice: Subject to any disclaimer, the term of this patent is extended or adjusted under 35 U.S.C. 154(b) by 491 days.

(21) Appl. No.: 16/800,715

(22) Filed: Feb. 25, 2020

(65) Prior Publication Data
US 2020/0272919 A1 Aug. 27, 2020

Related U.S. Application Data

(60) Provisional application No. 62/825,338, filed on Mar. 28, 2019, provisional application No. 62/810,700, filed on Feb. 26, 2019.

(51) Int. Cl.
*G16H 50/50* (2018.01)
*G16H 10/60* (2018.01)
(Continued)

(52) U.S. Cl.
CPC .............. *G06N 5/04* (2013.01); *G06N 5/02* (2013.01); *G06N 20/00* (2019.01); *G16H 10/20* (2018.01);
(Continued)

(58) Field of Classification Search
CPC ........ G16H 50/50; G16H 10/60; G16H 50/70; G16H 10/20
See application file for complete search history.

(56) References Cited

U.S. PATENT DOCUMENTS

| | | | |
|---|---|---|---|
| 2003/0144798 A1* | 7/2003 | Gardner ................. | G16Z 99/00 702/19 |
| 2004/0193450 A1* | 9/2004 | Knapp ................... | G16H 15/00 600/300 |

(Continued)

OTHER PUBLICATIONS

Hayward, John, "Knowledge Discovery in Clinical Performance of Cancer Patients," IEEE International Conference on Bioinformatics and Biomedicine, 2008 (Year: 2008).*

(Continued)

*Primary Examiner* — John P Go
(74) *Attorney, Agent, or Firm* — Finnegan, Henderson, Farabow, Garrett & Dunner, LLP (57) ABSTRACT

A model-assisted system for predicting survivability of a patient may include at least one processor. The processor may be programmed to access a database storing a medical record for the patient. The medical record may include at least one of structured and unstructured information relative to the patient and may lack a structured patient ECOG score. The processor may be further programmed to analyze at least one of the structured and unstructured information relative to the patient; based on the analysis, and in the absence of a structured ECOG score, generate a performance status prediction for the patient; and provide an output indicative of the predicted performance status. The analysis of at least one of the structured and unstructured information and the generation of the predicted performance status may be performed by at least one of a trained machine learning model or a natural language processing algorithm.

31 Claims, 7 Drawing Sheets

(51) Int. Cl.
    *G16H 50/70*    (2018.01)
    *G16H 10/20*    (2018.01)
    *G06N 5/04*    (2006.01)
    *G06N 20/00*    (2019.01)
    *G06N 5/02*    (2006.01)

(52) U.S. Cl.
    CPC ............. *G16H 10/60* (2018.01); *G16H 50/50* (2018.01); *G16H 50/70* (2018.01)

(56) References Cited

U.S. PATENT DOCUMENTS

| | | | |
|---|---|---|---|
| 2009/0234627 A1* | 9/2009 | Yu | A61N 5/1031 703/11 |
| 2016/0026917 A1* | 1/2016 | Weisberg | G06N 7/005 706/46 |
| 2016/0180041 A1* | 6/2016 | Pestian | G16H 20/40 705/2 |
| 2017/0091320 A1* | 3/2017 | Psota | G06F 16/313 |
| 2018/0300640 A1* | 10/2018 | Birnbaum | G16H 10/60 |
| 2018/0322961 A1* | 11/2018 | Kim | G16H 80/00 |
| 2018/0330824 A1* | 11/2018 | Athey | G16H 50/70 |
| 2019/0034590 A1 | 1/2019 | Oren et al. | |

OTHER PUBLICATIONS

International Search Report, issued from the European Patent Office in International Application No. PCT/US2020/019663, dated Jun. 2, 2020 (15 pages).

Riccardo Miotto et al, "Deep Patient: An Unsupervised Representation to Predict the Future of Patients from the Electronic Health Records", Scientific Reports, vol. 6, No. 1, May 17, 2016.

Benjamin Shickel et al, "Deep EHR: A Survey of Recent Advances in Deep Learning Techniques for Electronic Health Record (EHR) Analysis", ArXiv.org, Cornell University Library, Jun. 12, 2017.

\* cited by examiner

PROGNOSTIC SCORE BASED ON HEALTH INFORMATION

CROSS REFERENCES TO RELATED APPLICATIONS

This application claims the benefit of priority of U.S. Provisional Application No. 62/810,700, filed on Feb. 26, 2019, and U.S. Provisional Application No. 62/825,338, filed on Mar. 28, 2019. The entire contents of the foregoing application are incorporated herein by reference in their entirety.

BACKGROUND

Technical Field

The present disclosure relates to a model-assisted system and method for predicting survivability of a patient.

Background Information

In treating patients with potentially terminal medical conditions, doctors often make difficult assessments of their patients' wellbeing and likelihood of improvement. These prognosis determinations are often determinative of the appropriate treatment plan for the patient. Assessing a patient's likelihood of improvement or survivability may involve consideration of a combination of a multitude of factors, many of which are subjective and not easily measurable. Therefore, a need exists for a more quantifiable assessment of a patient's likelihood of death, short term improvement, and overall well-being to help determine an appropriate treatment plan.

Some solutions have been developed that attempt to quantify a patient's general well-being. For example, an Eastern Cooperative Oncology Group (ECOG) score is a prognostic score that enables physicians to track a patient's level of functioning (0-5; 0 is well; 5 is deceased). This score may help when assessing a patient's ability to tolerate certain therapies. For example, a patient with an ECOG score of 1 may be more freely prescribed a more toxic drug than a patient with an ECOG score of 4. However, development of ECOG scores depends on assessments from individual doctors. In practice, many doctors and clinicians do not track EGOG scores, which can make real world analysis of medical data difficult as ECOG score information may be absent or incomplete for a patient group. Further, these ECOG scores are subjective and depend on the individual judgment of each doctor assessing the patient. Accordingly, the ECOG score for a given patient may vary depending on the doctor providing the assessment.

Thus, there is a need to for an improved prognostic evaluation of patients, especially where an ECOG score is absent. Solutions should advantageously allow for development of a prognostic score based on data associated with a patient, without involving score assessments made by individual care providers. Solutions should be able to score a patient based on a wide range of data associated with the patient such as, for example, data from the patient's medical record. Solutions should further allow additional prognosis beyond a survivability score, such as predicting the patient's response to a particular treatment or assessing the patient's suitability for a clinical trial.

SUMMARY

Embodiments consistent with the present disclosure include systems and methods for predicting survivability of a patient. In an exemplary embodiment, there may be a model-assisted system for predicting a performance status of a patient comprising a least one processor. The processor may be programmed to access a database storing a medical record for the patient, the medical record including at least one of structured and unstructured information relative to the patient, wherein the medical record lacks a structured patient ECOG score; analyze at least one of the structured and unstructured information relative to the patient; based on the analysis, and in the absence of a structured ECOG score, generate a performance status prediction for the patient; and provide an output indicative of the predicted performance status of the patient, wherein the analysis of at least one of the structured and unstructured information relative to the patient and the generation of the predicted performance status for the patient are performed by at least one of a trained machine learning model or a natural language processing algorithm.

According to another disclosed embodiment, a method may be implemented for predicting a performance status of a patient. The method may comprise accessing a database storing a medical record for the patient, the medical record including at least one of structured and unstructured information relative to the patient, wherein the medical record lacks a structured patient ECOG score; analyzing at least one of the structured and unstructured information relative to the patient; based on the analysis, and in the absence of a structured ECOG score, generating a performance status prediction for the patient; and providing an output indicative of the predicted performance status of the patient, wherein the analysis of at least one of the structured and unstructured information relative to the patient and the generation of the predicted performance status for the patient are performed by at least one of a trained machine learning model or a natural language processing algorithm.

According to another disclosed embodiment, a system for providing a performance status score for a patient may comprise at least one processor. The at least one processor may be programmed to access a database storing a medical record for the patient, the medical record including structured and unstructured information relative to the patient; identify, based on the medical record, a line of treatment associated with the patient, wherein the structured information lacks a performance status score for the patient associated with the line of treatment; analyze the unstructured information to determine a performance status score for the patient associated with the line of treatment, wherein the performance status score is determined by at least one of a trained machine learning model or a natural language processing algorithm; and provide an output indicative of the performance status score.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings.

DETAILED DESCRIPTION

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for predicting a performance status of a patient. A user of the disclosed systems and methods may encompass any individual who may wish to access a patient's clinical experience and/or analyze patient data. Thus, throughout this disclosure, references to a "user" of the disclosed systems and methods may encompass any individual, such as a physician, a quality assurance department at a health care institution, and/or the patient. While reference is made to tumors or cancer therapies throughout this disclosure, these are provided as an example only, and it is understood that the disclosed systems and methods may apply to various other diseases and/or treatments.

Figure 1:
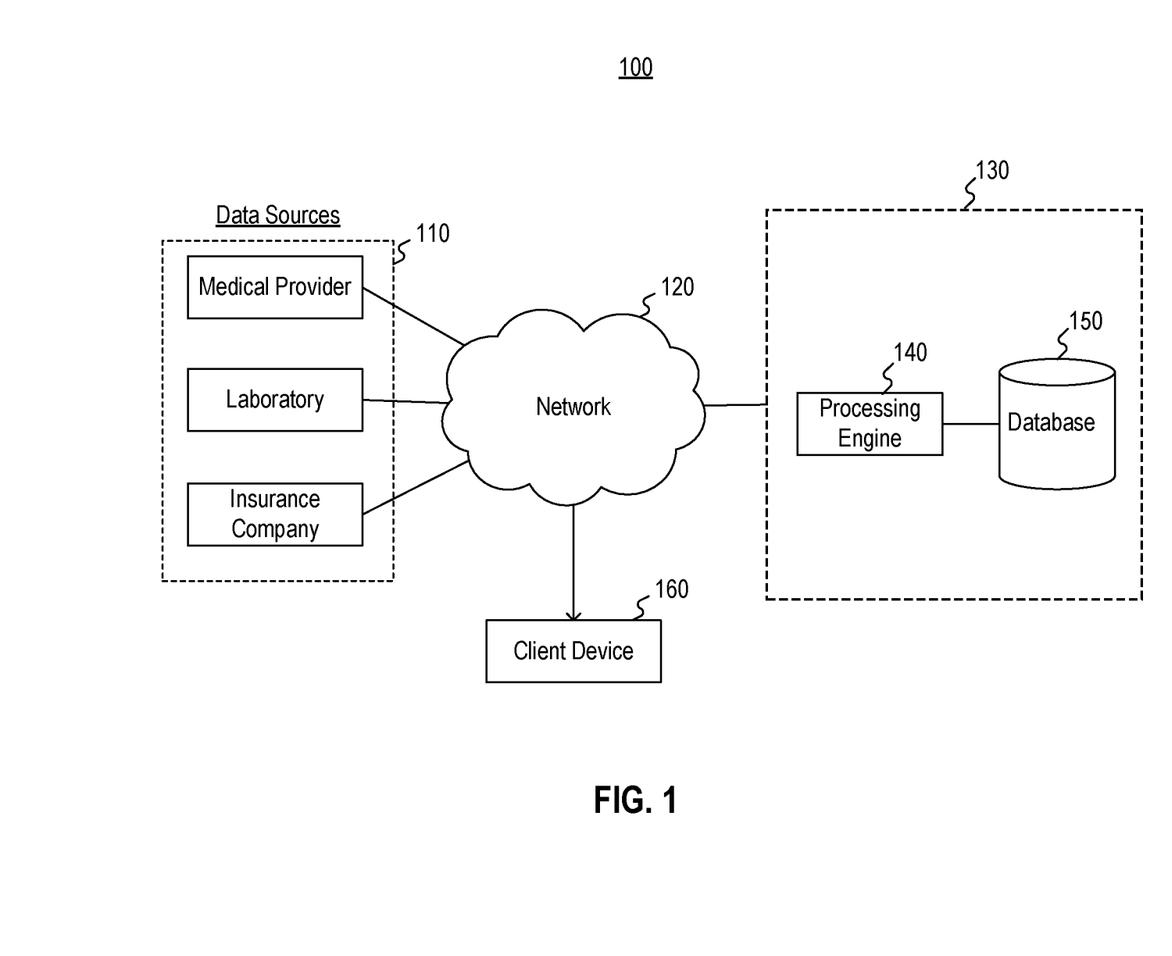
FIG. 1 is a block diagram illustrating an exemplary system environment for implementing embodiments consistent with the present disclosure.

FIG. 1 illustrates an exemplary system environment 100 for implementing embodiments consistent with the present disclosure, described in detail below. As shown in FIG. 1, system environment 100 includes several components. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 includes a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 140 and one or more databases 150, which are illustrated in a region bounded by a dashed line representing system 130 in FIG. 1. Processing engine 140 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

In one embodiment, system 130 may transmit and/or receive patient medical data to/from various other components, such as one or more data sources 110 and client device 160. The medical data may be stored in one or more medical records, each medical record associated with a patient. More specifically, system 130 may be configured to receive and store the data transmitted over a network 120 (e.g., the Internet, an Intranet, WAN, LAN, cellular network, Bluetooth, etc.) from various data sources, including data sources 110, process the received data, and transmit data and results based on the processing to client device 160.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

As described further below, system 130 may be configured to receive patient medical records from data sources 110 or other sources in network 120. Data sources 110 may include a variety of sources of medical data for a patient. For example, data sources 110 may include medical care providers of the patient, such as physicians, nurses, specialists, consultants, hospitals, clinics, and the like. Data sources 110 may also include laboratories such as radiology or other imaging labs, hematology labs, pathology labs, etc. Data sources 110 may also include insurance companies or any other sources of patient data. System 130 may be configured to develop one or more models to predict data about the patient. For example, system 130 may use machine learning techniques to develop a model based on training data. System 130 may apply the one or more models to the received medical results to generate prognostic results including, for example, survivability scores and other performance status indicators relating to the patient's treatment or well-being.

System 130 may further communicate with one or more client devices 160 over network 120. For example, system 130 may provide prognostic results based on analysis of data from data sources 110 to client device 160. Client device 160 may include any entity or device capable of receiving or transmitting data over network 120. For example, client device 160 may include a computing device, such as a server or a desktop or laptop computer. Client device 160 may also include other devices, such as a mobile device, a tablet, a wearable device (i.e., smart watches, implantable devices, fitness trackers, etc.), a virtual machine, an IoT device, or other various technologies. In some embodiments, client device 160 may transmit queries for information about a patient over network 120 to system 130, such as a query for a prognostic score, patient medical records or various other information about a patient.

Figure 2:
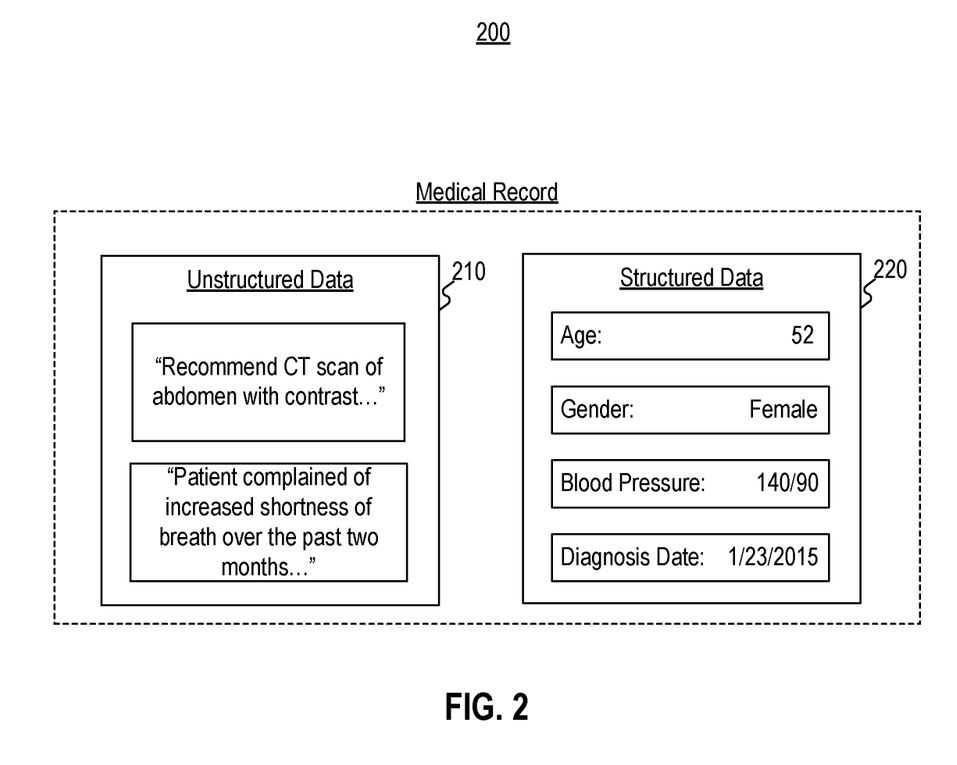
FIG. 2 is a block diagram illustrating an exemplary medical record for a patient consistent with the present disclosure.

FIG. 2 illustrates an exemplary medical record 200 for a patient. Medical record 200 may be received from data sources 110 and processed by system 130, as described above. The records received from data sources 110 (or elsewhere) may include both structured data 210 and unstructured data 220, as shown in FIG. 2. Structured data 210 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient. Unstructured data may include information about the patient that is not quantifiable or easily classified, such as physician's notes or the patient's lab reports. Unstructured data 220 may include information such as a physician's description of a treatment plan, notes describing what happened at a visit, descriptions of how patient is doing, radiology reports, pathology reports, etc. In some embodiments, the unstructured data may be captured by an abstraction process, while the structured data may be entered by the health care professional or calculated using algorithms.

In the data received from data sources 110, each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases. In some embodiments, the records may be stored and/or provided a plurality of electronic data representations. For example, the patient records may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

Figure 3:
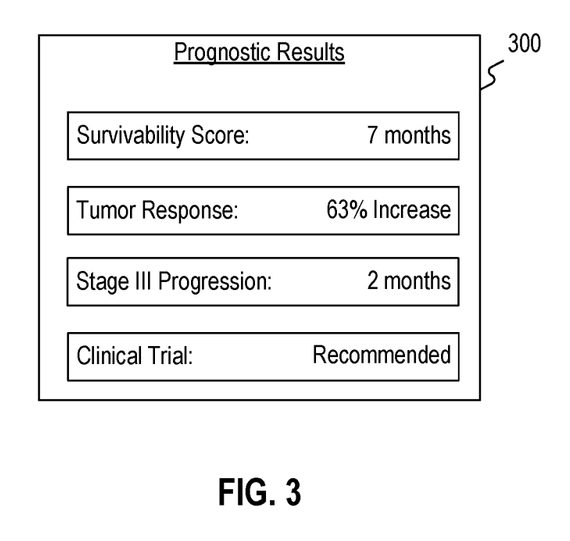
FIG. 3 is a block diagram illustrating an exemplary prognosis prediction for a patient consistent with the present disclosure.

FIG. 3 illustrates exemplary prognosis results 300 for a patient consistent with the present disclosure. For example, prognosis results 300 may be generated by system 130 by applying a model to patient medical data received from data sources 110. Prognosis results 300 may include a variety of different predictions about a patient based on medical record 200. For example, as shown in FIG. 3, prognostic results 300 may include a calculated survivability score. Because this score is based on machine learning techniques, the calculated score may serve as a better prediction of overall survivability than an ECOG score. In some embodiments, the survivability score may include a time estimate of how long the patient is expected to survive. For example, the survivability score may predict the survivability of a patient in months, as shown in FIG. 3. Any other appropriate time increment or interval may also be used. In some embodiments, the time estimate may be relative to a particular date, such as an initiation date of the patient's treatment or therapy. The survivability score may also be represented on a scale (e.g., ranging from 1-10 or 1-5) or as a percentage. While various forms or formats are described above, it is understood that the disclosed embodiments are not limited to any particular forms or formats of the survivability score.

Further, while a survivability score is provided by way of example, various other performance status indicators may be included in prognosis results 300. As used herein a "performance status" for a patient may include any indication of a patient's current health or well-being. The performance status is not limited to the survivability score of the patient and may include other indicators of the patient's status. As one example, the performance status may relate to the emotional or mental health of the patient. For example, based on analysis of notes taken by a physician, system 130 may determine whether a patient has a positive or negative outlook in response to a treatment, whether the patient shows signs of depression, whether the patient exhibits certain mental side-effects, or any other information regarding the patient's emotional well-being. Such information may be useful for determining appropriate treatment, determining whether the patient should be included in a clinical trial, or the like. The performance status may be represented as a score (e.g., a numerical value, a text-based classification, etc.), similar to the survivability score described above.

Prognosis results 300 may also include a variety of other performance status predictions associated with the patient's treatment, progression of the patient's disease, or the patient's overall well-being. In some embodiments, system 130 may generate a time estimate of expected improvement or worsening of the patient due to a disease. For example, prognosis results 300 may reflect an estimated timeframe for recovery for the patient. In other embodiments, prognosis results 300 may include a time estimate for worsening of the patient such as, for example, the time it will take for a cancer treatment patient to reach advanced stages of the disease. These time estimates may be relative to an initiation date of a particular treatment or therapy for the patient, or other dates related to the patient's care. The performance status prediction may include other predictions regarding the patient, such as a predicted likelihood of recovery, a predicted responsiveness to a particular treatment, a predicted susceptibility to a particular disease, a predicted complication or other event that may occur, or various other predictions regarding the patient's well-being.

Prognosis results 300 may also include a suitability of including the patient in a clinical trial. For example, system 130 may determine the patient's suitability for one or more clinical trials based on a generated performance status indication, such as a generated survivability score, or other factors used in the machine learning process. The clinical trial may involve treating the patient using a particular therapy or technique. For example, this may include an innovative cancer therapy or an experimental drug treatment. The patient's suitability output may be represented in the prognosis results in a binary "recommended" or "not recommended" format, as shown in FIG. 3. Alternatively, the patient's suitability may be represented in a graduated format, such as on a scale (e.g. from 1-10), as a percentage, a range of classifications (e.g. "highly suitable," "moderately suitable," etc.), or in various other formats. In some embodiments, the patient's suitability for inclusion in the clinical trial may be based on the survivability score generated by system 130. A patient with a longer predicted survivability, for example, may be more likely to be included in the clinical trial.

Prognosis results 300 may also include a predicted response for a patient's disease, either untreated or in response to particular therapy. For example, in treating a cancer patient, system 130 may generate a size estimate indicative of how much a tumor in the patient is predicted to shrink or grow over a predetermined time period. In some embodiments, a prediction of the tumor's size may be determined based on a predetermined time after an initiation date of a therapy. The tumor response estimate may be represented as a percentage increase or percentage decrease in size (either by weight, by volume, or by some other unit of measurement) as shown in FIG. 3. The predicted tumor response may also be expressed in absolute terms, such as by weight, by volume, or as a length (e.g. diameter, circumference, etc.).

Figure 4:
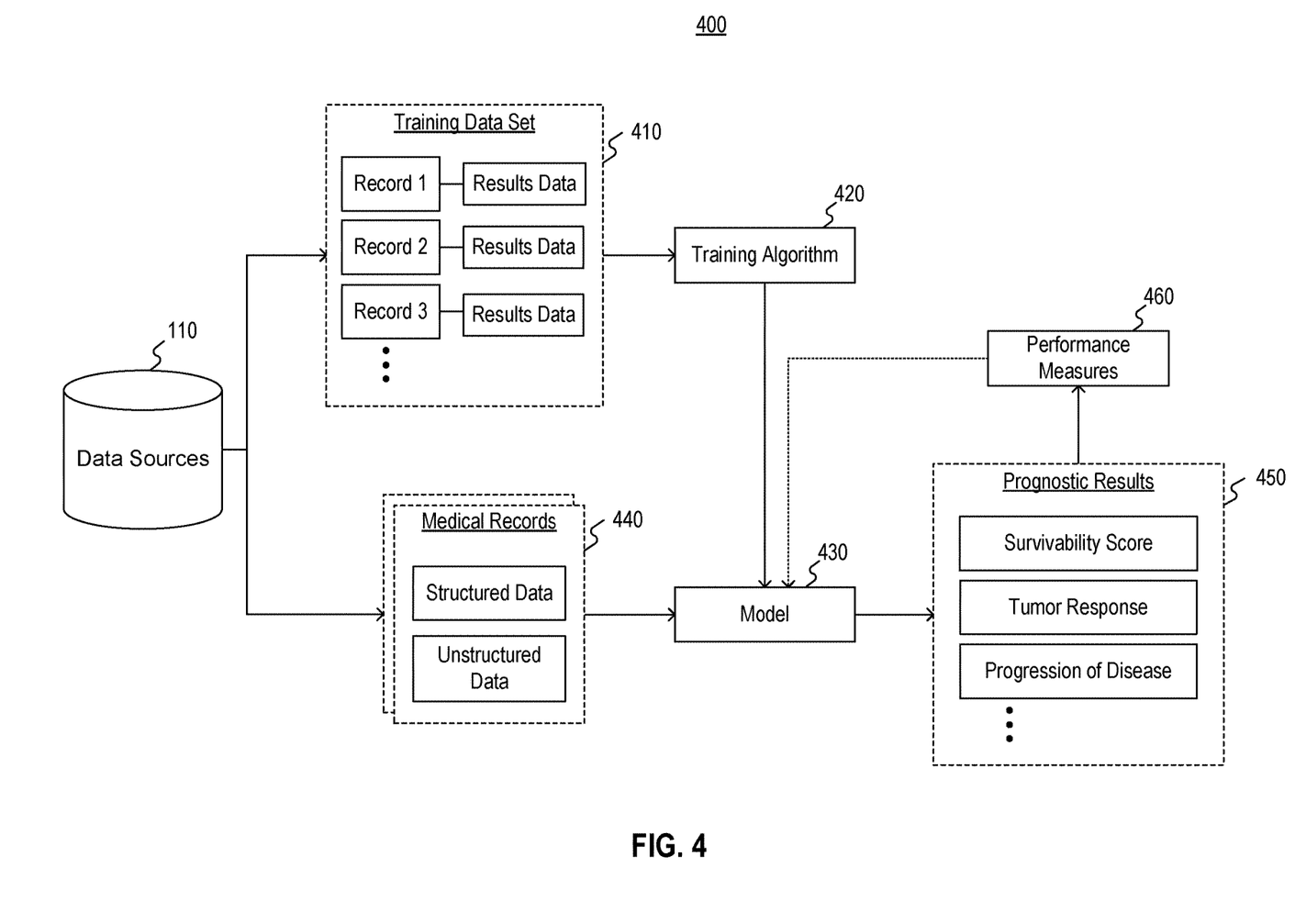
FIG. 4 is a block diagram illustrating an exemplary machine learning process for implementing embodiments consistent with the present disclosure.

FIG. 4 illustrates an exemplary machine learning system 400 for implementing embodiments consistent with the present disclosure. Machine learning system 400 may be implemented as part of system 130 (FIG. 1). For example, machine learning system 400 be a component or process of processing engine 140. In accordance with the disclosed embodiments, machine learning system 400 may generate a trained model (e.g., a supervised machine learning system) based on a set of training data associated with a patient, and may use the model to generate a survivability score or a number of other predictions related to the patient. For example, as shown in FIG. 4, machine learning system 400 may generate a model 430 for generating prognostic results 300. Machine learning system 400 may develop model 430 through a training process, for example, using training algorithm 420.

Training of model 430 may involve the use of a training data set 410, which may be input into training algorithm 420 to develop the model. Training data 410 may include a plurality of patient medical records (e.g., "Record 1," "Record 2," "Record 3," etc., as shown in FIG. 4) for which various results that are to be estimated by the model are already known (e.g. patient survivability, patient performance status, tumor response, disease progression timeframes, suitability for a clinical trial, etc.). In some embodiments, training data 410 may also be cleaned, conditioned and/or manipulated prior to input into training algorithm 420 to facilitate the training process. Machine learning system 400 may extract one or more features (or feature vectors) from the records to determine correlations between the features and a particular patient result. These features may be extracted from the structured and unstructured data within the medical records described above. For example, the training process may correlate data such as the patient's weight, gender, recorded vital signs, diagnosis code, etc., with an associated survivability of the patient or other result.

For unstructured data, various techniques may be used to provide feature vectors to the model (e.g., natural language processing techniques). While some or part of the documents of a patient's medical records may be available electronically, typed, handwritten, or printed text in the records may be converted into machine-encoded text (e.g., through optical character recognition (OCR)). The electronic text may be searched for certain key words or phrases associated with a particular result. In some embodiments, a snippet of text in a vicinity of the identified word or text may be tested to glean additional information about the context of the word or phrase. For example, when searching for term "metastatic," the phrase "no evidence of metastatic activity" may convey a significantly different meaning from "stage IV; metastatic." By analyzing the snippet of text surrounding words or phrases of interest, one or more features may be extracted, forming a feature vector that may be provided as input to the trained selection model. These features from the unstructured documents may be combined with features from structured data associated with the patient's medical record or other available data sources (e.g., claims data, patient-reported data).

A portion of the extracted features along with information about the desired outcome (e.g., the patient's survivability) may be stored as training data 410. Then, training data 410 (or a certain portion of the data) may be placed through a training algorithm 420 to train the model. Through exposure to many such instances, model 430 may "learn" and provide outputs identical to or close to the expected results.

The machine learning system 400 may employ any suitable machine learning algorithms to develop model 430. For example, training algorithm 420 may include logistic regression that generates one or more functions (or rules) that relate extracted features to particular patient results. Additionally, or alternatively, training algorithm 420 may include one or more neural networks that adjust weights of one or more nodes such that an input layer of features is run through one or more hidden layers and then through an output layer of patient results (with associated probabilities). Other types of machine learning techniques may also be used, either in combination with or separate from the logistic regression technique, such as a linear regression model, a lasso regression analysis, a random forest model, a K-Nearest Neighbor (KNN) model, a K-Means model, a decision tree, a cox proportional hazards regression model, a Naïve Bayes model, a Support Vector Machines (SVM) model, or gradient boosting algorithms. The models may also be developed using an unsupervised or reinforcement machine learning process, where manual training is not required.

A remaining portion of training data 410 may be used to test the trained model 430 and evaluate its performance. For example, for each individual in the remainder of training data set 410, feature vectors may be extracted from the medical records associated with that patient. Those feature vectors may be provided to model 430, and the output for that individual may be compared to the known outcome for that individual (for example, that individual's actual survival time). Deviations between the output of model 430 and the known outcomes for any individuals in training data set 410 may be used to generate performance measures 460, as shown in FIG. 4. Performance measures 460 may be used to update model 430 (e.g., retrain the model) to reduce deviations between the prognostic results 450 and the known patient results. For example, one or more functions of the model may be added, removed, or modified (e.g., a quadratic function may be modified into a cubic function, an exponential function may be modified into a polynomial function, or the like). Accordingly, the deviations may be used to inform decisions to modify how the features passed into model 430 are constructed or which type of model is employed. As an alternative, in some embodiments, one or more weights of the regression (or, if the model comprises a neural network, one or more weights of the nodes) may be adjusted to reduce the deviations. Where the level of deviation is within a desired limit (e.g., 10%, 5%, or less), one or more models 430 may be deemed suitable for operating on a data set for which patient results are unknown.

Although described above in terms of "deviations," one or more loss functions may also be used to measure the accuracy of the model. For example, a square loss function, a hinge loss functions, a logistic loss function, a cross entropy loss function, or any other loss function may be used. In such embodiments, the updates to the model may be configured to reduce (or even minimize, at least locally) the one or more loss functions.

Once model 430 is constructed, new data, such as medical records 440, may be input to models 430. Medical records 440 may correspond to medical record 200, as described above. For example, medical records 440 may include structured and unstructured data associated with a plurality of patients, such that each patient is associated with one or more medical records. Model 430 may extract features from medical records 440 to produce scores and/or predictions, such as prognostic results 450. Prognostic results 450 may contain a survivability score as well as other scores or predictions, as described above with respect to prognostic result 300.

In some embodiments, unstructured data 210 and structured data 220 may be analyzed using one or more natural language processing algorithms. As used herein, "natural language processing" may refer to any technique or process for analyzing and processing written natural language information. Natural language information may include text or speech data generated by a human through a written or spoken language. For example, the natural language information may be included as unstructured data in a medical record, which may be analyzed as described above. The natural language processing algorithms may include any computer-based techniques for analyzing the natural language information. For example, the natural language processing algorithms may include techniques such as lemmatization, part-of-speech tagging, sentence breaking, word stemming, lexical semantics, machine translation, name entity recognition (NER), optical character recognition (OCR), or various other techniques that may facilitate extracting information from the unstructured or structured data. These algorithms may be used alone or in combination with the machine learning techniques described above. For example, the natural language processing algorithms may be used as part of the conditioning of unstructured data described above.

Figure 5:
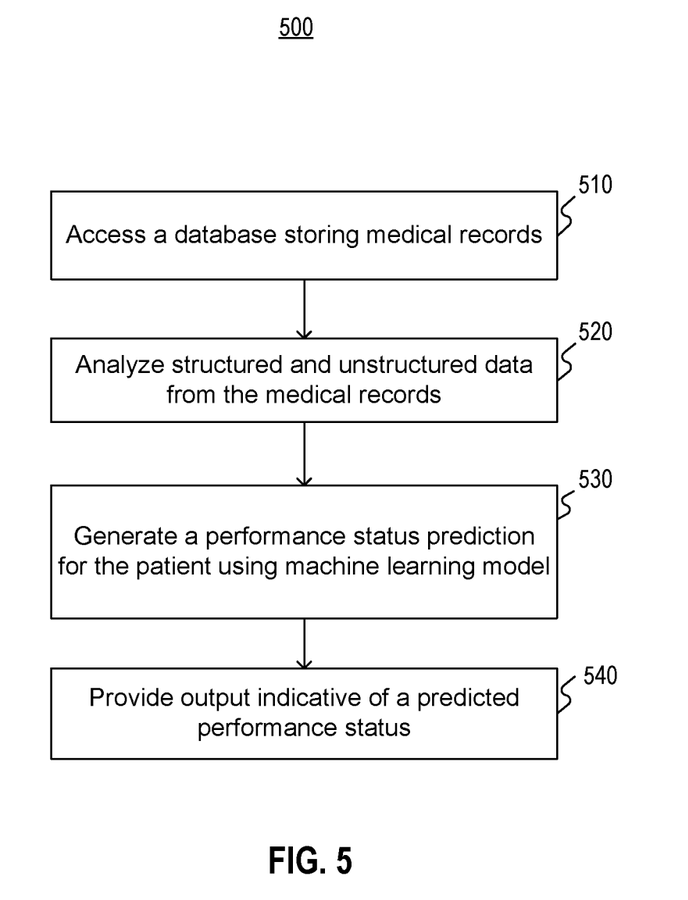
FIG. 5 is a flowchart illustrating an exemplary method for predicting a performance status for a patient consistent with the present disclosure.

FIG. 5 illustrates an exemplary method 500 for generating a performance status for a patient. Method 500 may be implemented, for example, by at least one processor of processing engine 140 of system 100, shown in FIG. 1.

At step 510, method 500 may include accessing a database storing a medical record for the patient. The medical record may include at least one of structured and unstructured information relative to the patient. For example, processing engine 140 may access a database through network 120 from data sources 110 or other various sources. As described above, data sources 110 may include various sources of patient medical data including, for example, the medical record for the patient may be received from a medical provider, a laboratory or an insurance company. Alternatively, or in addition, processing engine may access a local database such as database 150.

Processing engine 140 may access one or more medical records consistent with medical record 200, as described above. The medical record may comprise one or more electronic files, such as text files, image files, PDF files, XLM files, YAML files, or the like. The medical record may contain structured information, which may include a gender, a birth date, a race, a weight, a lab result, a vital sign, a diagnosis date, a visit date, a medication order, a diagnosis code, a procedure code, a drug code, a prior therapy, or a medication administration, and unstructured information, which may include text written by a health care provider, a radiology report, or a pathology report. Each medical record may be associated with a particular patient and, in some embodiments, multiple medical records may be associated with a particular patient. The medical record may not be limited to data from medical institutions and may include other related forms of data, such as claims data (e.g., from an insurance company), patient-reported data, or other information associated with the patient's treatment or well-being. Consistent with the disclosed embodiments, the medical record may lack a patient ECOG score. In some embodiments the medical record may lack a structured ECOG score. For example, the ECOG score may not be included in the structured information but may be included in unstructured information. In other embodiments, the medical record may lack an ECOG score in both the structured and unstructured information.

At step 520, method 500 may include analyzing at least one of the structured and unstructured information relative to the patient. In some embodiments, analysis of at least one of the structured and unstructured information relative to the patient and the generation of the predicted performance status of the patient may be performed by a trained machine learning model. For example, processing engine 140 may employ a machine learning technique to analyze the medical record of the patient, as described above. Step 520 may use one or more trained machine learning models developed through a machine learning process, as described in relation to FIG. 4. For example, the trained models may include a logistic regression model, a neural network, a cox proportional hazards regression, a lasso regression analysis network, or a random forest model. Similarly, the natural language processing algorithm may include one or more of a logistic regression, a neural network, a cox proportional hazards regression, a lasso regression analysis network, or a random forest algorithm. In some embodiments, models may also be developed using an unsupervised or reinforcement machine learning process, where manual training is not required. In other embodiments, the analysis of at least one of the structured and unstructured information relative to the patient and the generation of the predicted performance status for the patient may be performed by a natural language processing algorithm. For example, step 520 may include using a natural language processing algorithm on the structured or unstructured data to extract information indicating a tumor response, a response to a prescribed treatment, an improvement or worsening of a patient's condition, or any other text-based information that may indicate a performance status of a patient.

Step 520 may include additional sub-steps to facilitate analysis of the medical record, such as conditioning or altering information in the record. Processing engine 140 may employ various techniques to interpret the structured or unstructured information. Typed, handwritten, or printed text in the records may be converted into machine-encoded text (e.g., through optical character recognition (OCR)). The electronic text may be searched for certain key words or phrases associated with a particular result and snippets of text in a vicinity of the identified word or text may be tested to glean additional information about the context of the word or phrase, as described above. Processing engine 140 may also extract one or more feature vectors from the medical record, as described above. Process engine 140 may input the medical record (or extracted features) into the trained machine learning model.

At step 530, method 500 may include generating a performance status prediction for the patient based on the analysis. As discussed, the analysis may be performed in the absence of a structured ECOG score. In some embodiments, the performance status prediction may comprise a survivability prediction for the patient. For example, processing engine 140 may generate a survivability score as described above with respect to FIG. 3. The survivability prediction may indicate an estimated duration of the patient's survival. For example, the survivability prediction may include a time estimate of how long the patient is expected to survive. In some embodiments, the time estimate of how long the patient is expected to survive may be relative to an initiation date of a therapy, such as the administration of a drug or initiation of a particular cancer treatment. The survivability score may also be presented in various other formats. The predicted performance status is not limited to a survivability score, and may include other indicators of the patient's status, such as the current stage of treatment the patient is in, an assessment of the patient's current health or condition, a patient's response to a particular treatment, the patient's susceptibility to a certain disease, a patient's emotional or mental health, or various other status indicators. These predicted performance statuses may be assigned a score, similar to the survivability scores described in detail above.

In some embodiments, the performance status prediction may be generated in step 530 using one or more machine learning models, as with step 520. For example, processing engine 140 may input data associated with the medical record accessed in step 510 into trained machine learning model 430. The model may output a set of prognostic results including the performance status of the patient associated with the medical record. In some examples, the prognostic results may include a survivability score or other performance status score as discussed above.

At step 540, method 500 may include providing an output indicative of the predicted performance status of the patient. For example, system 130 may transmit the predicted performance status to another device or entity in network 120. In some embodiments, system 130 may transmit the predicted performance status (e.g., a survivability score) to a client device, such as a computer, server, or mobile device. Alternatively, or additionally, system 130 may transmit the prediction to data sources 110, for example, to a medical provider supplying the medical record. Processing engine 140 may also generate a report or other compilation of information including the performance status prediction. The performance status prediction may also be presented locally, for example on a display associated with system 130. For example, a survivability score (or other indicator of performance) may be displayed as a numeric value, as text (e.g., a description of time period such as "the patient is expected to survive two years"), a graphic, such as a timeline or other pictorial representation, a combination of text and graphics, or any other manner of presenting the information.

Method 500 may further include additional steps. For example, additional results or predictions may be generated in addition to or instead of the predicted performance status. In some embodiments, method 500 may further include determining a suitability of including the patient in a clinical trial based on at least the output indicative of the predicted performance status of the patient. As described above, the performance status may be helpful in assessing a patient's suitability for inclusion in a clinical trial. For example, a patient predicted to survive longer (as determined by a survivability prediction) may be more likely to be included in a clinical trial. Other performance status indicators or scores, such as the condition of the patient, the emotional or mental condition of the patient, or other status indicators may similarly be useful in determining suitability for inclusion in a clinical trial. In some embodiments, for example, the clinical trial may involve treating the patient using a therapy, such as a cancer therapy. Method 500 may also include providing an output indicating the suitability of including the patient in the clinical trial, similar to the output of step 540.

Other predictions may also be generated based on the information included in the medical records as part of method 500. For example, method 500 may further include generating a time estimate of an expected improvement or worsening of the patient due to a disease based on the analysis of at least one of the structured and unstructured information relative to the patient, as described above. This time estimate may be relative to a particular date, such as an initiation date of a therapy for the patient. In some embodiments, method 500 may further include generating a size estimate indicative of how much a tumor in the patient is predicted to shrink or grow over a predetermined time period after an initiation date of a therapy based on the analysis of at least one of the structured and unstructured information relative to the patient.

Figure 6:
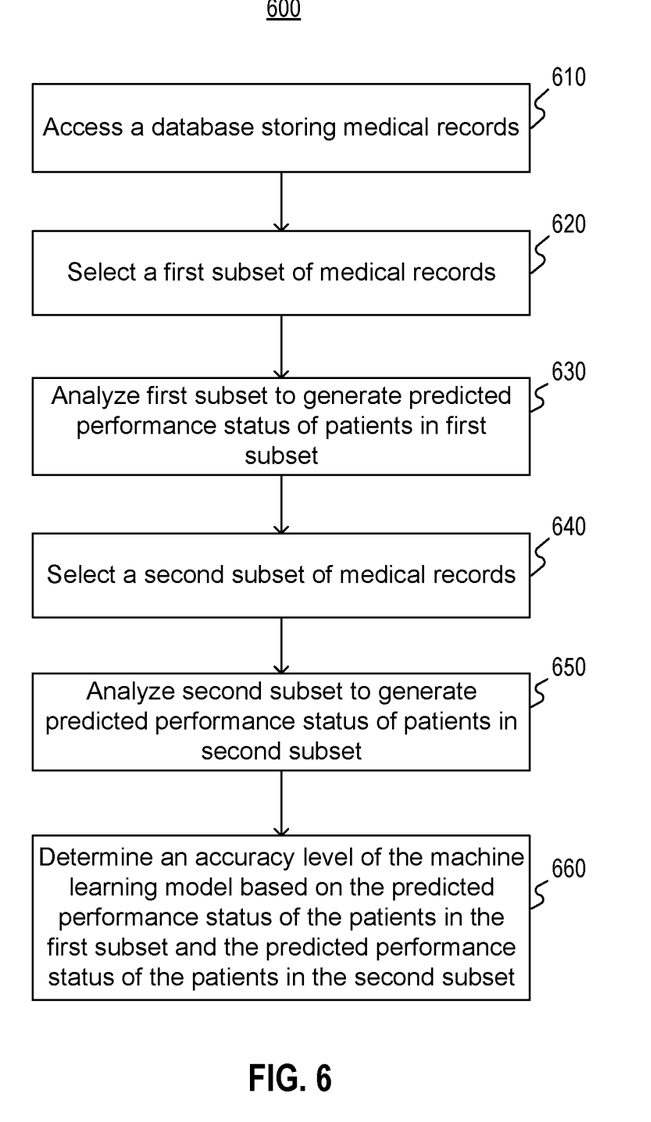
FIG. 6 is a flowchart illustrating an exemplary method for determining an accuracy level of a trained machine learning model consistent with the present disclosure.

FIG. 6 illustrates an exemplary method 600 for determining an accuracy level of a trained machine learning model. Method 600 may be implemented, for example, by at least one processor of processing engine 140 as part of training of a machine learning model. The determined accuracy level may be used to modify (e.g., re-train) the model to improve the accuracy.

At step 610, method 600 may include accessing medical records for a plurality of patients. The medical records may be accessed, for example, from a database storing medical records, such as database 150. In some embodiments, the medical records may be accessed through a network, for example from data sources 110. In other embodiments, the medical records may be provided as part of a training data set for training/testing a machine learning model, as described above. The medical records may be associated with a set of patients and may contain structured and unstructured information as described above. The medical records may also lack patient ECOG scores (e.g., structured and/or unstructured ECOG scores).

At step 620, method 600 may include selecting a first subset of the medical records accessed in step 610. For example, a subset of the patients associated with the medical records may be identified and those records associated with that subset of patients may be selected. At step 630, method 600 may include analyzing the first subset of the medical records to generate a predicted performance status of the patients in the first subset. In some embodiments, the predicted performance status may comprise a predicted survivability for the patients, as described above. The analysis of the medical records may be consistent with steps 520 and 530, described above in reference to method 500. For example, the subset of medical records may be analyzed to identify and/or isolate information from the structured and unstructured information and extract features or feature vectors. The medical records (or the features or feature vectors) may then be input into a trained machine learning model, which may output a predicted performance status score of the patients in the first subset. Similar to method 500, the performance status prediction may be represented in a variety of formats, including an estimated time of survivability of the patient.

At step 640, method 600 may include selecting a second subset of the medical records, wherein the second subset does not include the first subset. For example, a second subset may be selected such that none of the medical records included in the first subset are included in the second subset. At step 650, method 600 may include analyzing the second subset of the medical records to generate a predicted performance status of the patients in the second subset. The second subset of medical records may be analyzed via a machine learning model to produce a performance status score or other indicator, similar to the first subset in step 630.

At step 660, method 600 may include determining an accuracy level of the trained machine learning model based on the predicted performance status of the patients in the first subset and the predicted performance status of the patients in the second subset. Step 660 may include comparing the predicted performance status of the first and second subsets to a known performance status of the patients associated with the subsets of medical records. For example, if the medical records accessed in step 610 are part of a training or testing data set, the actual performance status of the patients may already be known. A system performing method 600 may determine the accuracy of the trained machine learning model based on deviations between the predicted and known patient performance status values. One or more loss functions may also be used to measure the accuracy of the model, for example, using a square loss function, a hinge loss functions, a logistic loss function, a cross entropy loss function, or any other loss function.

The determined accuracy level of the trained machine learning model may be used to improve the model. For example, based on the determined accuracy levels, one or more functions or variables of the model may be added, removed, or modified, as described above. The determined accuracy levels may be used to inform decisions to modify how the features passed into the model are constructed or which type of model is employed. In some embodiments, one or more weights of the regression (or, if the model comprises a neural network, one or more weights of the nodes) may be adjusted to reduce the deviations. Where the level of deviation is within a desired limit (e.g., 10%, 5%, or less), one or more models may be deemed suitable for operating on a data set for which patient results are unknown, for example using method 500 described above.

The methods described above may be particularly useful when a medical record, such as medical record 200, does not contain a structured score (such as an ECOG score). For example, structured data 210 may not contain a field designating an ECOG score or other similar types of scores. In some embodiments, however, while medical record 200 may not include a structured ECOG score, it may include an ECOG score in unstructured data 210. For example, a physician or other medical professional may include handwritten notes such as "ECOG 1" or "patient status of 1" which may indicate that the patient has an ECOG score of 1. The disclosed systems may further be configured to extract patient status scores, such as ECOG scores, from unstructured patient medical data. The extracted ECOG score data may be used to assess a performance status of a patient alone or in combination with the techniques described above. In some embodiments, the extracted ECOG scores may be used to fill in missing ECOG score data in structured data 210.

The ECOG score may be extracted from unstructured data 220 using various techniques. For example, a simple search query may be performed on the unstructured data to identify an ECOG score. In some embodiments, a snippet approach may be used, similar to the snippets described above. For example, system 130 may search for documents or portions of documents containing a keyword term within a certain number of words of a number that may indicate an ECOG score (e.g., a number between 0 and 5). As an illustrative example, a query may be performed to fetch documents containing "ECOG" (or other similar terms, such as "performance status," "patient status," etc.) within 3 words of a number between 0 and 5. Various other ranges of words (e.g., more or less than 3 words) may be used. A regular expression, or various other machine learning algorithms, including those described above, may then be applied to the search results to extract numeric scores. The extracted structured scores may then be stored in a table or other format for use in further analysis associated with the patient. In some embodiments, the extracted ECOG scores may be stored in database 150.

In some embodiments, extraction of the ECOG score may be in relation to a particular line of treatment of the patient. As used herein, a "line of treatment" may refer to any cycle or process for treating a patient. For example, a line of treatment may include a drug treatment therapy, such as a complete cycle of a single drug or a combination of several drugs. As another example, a line of treatment may include a complete cycle of cancer treatment, such as a radiation therapy, or the like. The line of treatment is not limited to any particular form or therapy or treatment. System 130 may identify a series of lines of treatment for one or more patients from the medical records and may further identify lines of treatment that are missing baseline structured ECOG scores. The extraction of the ECOG scores may be performed on the unstructured data associated with the lines of treatment that are missing the baseline structured ECOG scores. In some embodiments, the search query performed on the unstructured information may be limited to a particular timeframe associated with the line of treatment. The timeframe may be any predetermined amount of time that may be likely to provide relevant search results for the particular line of treatment. For example, the search may be limited to a certain time period before a treatment start date (e.g., 2 months, 30 days, 15 days, etc.) and a certain time period after the treatment start date (e.g., 2 days, 7 days, 2 weeks, etc.).

Figure 7:
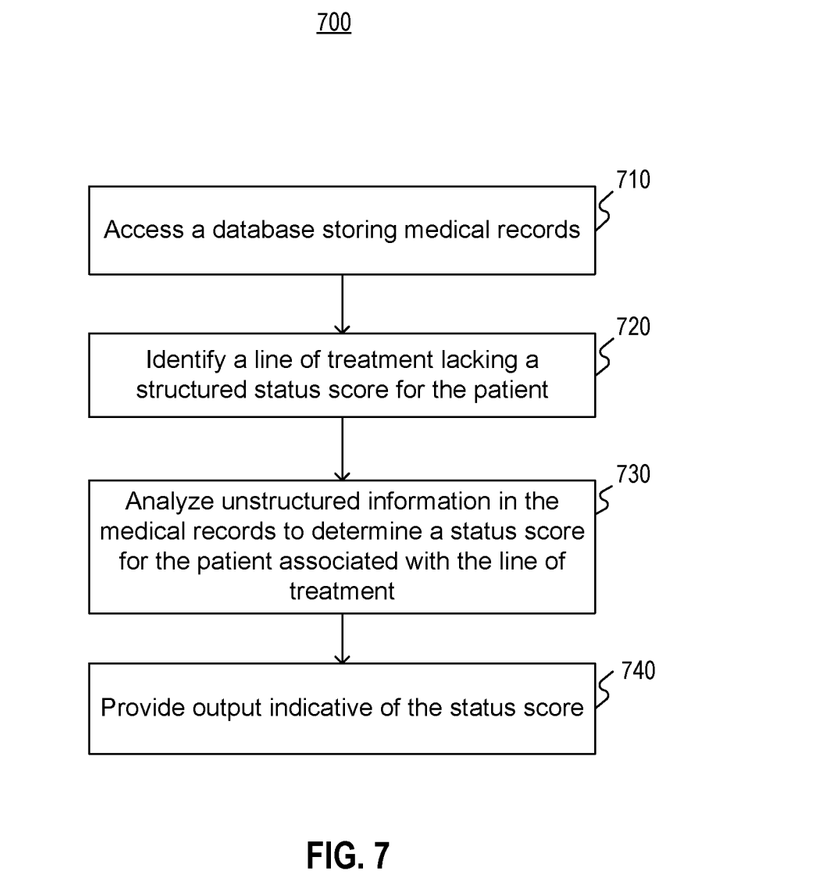
FIG. 7 is a flowchart illustrating an exemplary method for determining a patient performance status score consistent with the present disclosure.

FIG. 7 is a flowchart illustrating an exemplary method 700 for determining a patient status score consistent with the present disclosure. Method 700 may be implemented, for example, by at least one processor of processing engine 140 of system 100, shown in FIG. 1.

At step 710, method 700 may comprise accessing a database storing a medical record for a patient. For example, processing engine 140 may access a database through network 120 from data sources 110 or other various sources to obtain medical record 200. The medical record may include structured and unstructured information relative to the patient. For example, the medical record may include structured information 210 and unstructured information 220, as described above.

At step 720, method 700 may include identifying, based on the medical record, a line of treatment associated with the patient. As described above, the structured information in the medical record may lack a status score for the patient associated with the line of treatment. The status score may be any indicator of performance status for a patient. For example, in some embodiments, the status score may comprise an ECOG score for the patient.

At step 730, method 700 may include analyzing the unstructured information to determine a status score for the patient associated with the line of treatment. As described above, the analysis may include performing a search on the unstructured data to identify documents or portions of documents containing keywords within a certain number of words of a number. In some embodiments, the analysis of at the unstructured information and the generation of the predicted performance status for the patient may be performed by a trained machine learning model. For example, the keywords may include terms such as "ECOG" or "performance status." Documents in which the keyword appears within a certain number of words (e.g., 3 words, 5 words, etc.) of a number between 0 and 5 (or any other number range that may represent a status score) may be identified. A linear regression or other algorithm may be performed on the search results to extract the patient status score. In other embodiments, a natural language processing algorithm may be used to analyze the unstructured information as described above. In some embodiments, the analysis of the unstructured information may be limited to unstructured information recorded within a predefined timeframe of a start date of the line of treatment. For example, unstructured information recorded within 30 days before and 7 days after a start date of a line of treatment may be analyzed.

At step 740, method 700 may include providing an output indicative of the status score. The output may be provided using any of the various methods described above with respect to outputting the performance status of a patient. For example, system 130 may transmit the status score to another device or entity in network 120. In some embodiments, the status score may be stored, for example in database 150. In some embodiments, the status score may be stored in a table containing status scores for other lines of treatment missing baseline ECOG scores. In some embodiments, the status score may be output for display as part of a user interface displayed on a screen of a device.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted system for predicting a performance status of a first patient, the system comprising:
   at least one processor programmed to:
   access a database storing a plurality of medical records, wherein each medical record in the plurality of medical records comprises at least one of structured or unstructured information;
   extract a first feature from a subset of medical records in the plurality of medical records;
   train a machine learning model based on the first extracted feature, wherein training the machine learning model comprises correlating the first extracted feature with at least one known result for a second patient associated with the subset of medical records;
   extract a second feature from at least one medical record in the plurality of medical records, wherein the at least one medical record is associated with the first patient and lacks a structured ECOG score for the first patient;

input the second feature into the machine learning model to generate an ECOG score for the first patient; and generate, based at least in part on the generated ECOG score for the first patient, an output indicative of a suitability of the first patient for inclusion in a clinical trial.

2. The system of claim 1, wherein the machine learning model comprises at least one of a logistic regression model, a neural network, or a random forest model.

3. The system of claim 1, wherein the machine learning model comprises a cox proportional hazards regression model.

4. The system of claim 1, wherein the machine learning model applies a lasso regression analysis.

5. The system of claim 1, wherein the at least one medical record associated with the first patient is received from a medical care provider, a laboratory, or an insurance company.

6. The system of claim 1, wherein the at least one medical record associated with the first patient includes structured information on at least one of a gender, a birth date, a race, a weight, a lab result, a vital sign, a diagnosis date, a visit date, a medication order, a diagnosis code, a procedure code, a drug code, a prior therapy, or a medication administration.

7. The system of claim 1, wherein the at least one medical record associated with the first patient includes unstructured information comprising at least one of text written by a health care provider, a radiology report, or a pathology report.

8. The system of claim 1, wherein the at least one processor is further programmed to generate a survivability score for the first patient.

9. The system of claim 8, wherein:
the survivability score comprises a time estimate of how long the first patient is expected to survive; and
the at least one processor is further programmed to present the survivability score for the first patient.

10. The system of claim 9, wherein the time estimate of how long the first patient is expected to survive is relative to an initiation date of a therapy.

11. The system of claim 1, wherein the at least one processor is further programmed to present at least one of the generated ECOG score or the output indicative of the suitability of the first patient for inclusion in the clinical trial.

12. The system of claim 1, wherein the clinical trial involves treating the first patient using a therapy.

13. The system of claim 12, wherein the therapy is a cancer therapy.

14. The system of claim 1, wherein the at least one processor is further programmed to
generate a time estimate of expected improvement or worsening of the first patient due to a disease.

15. The system of claim 14, wherein the time estimate of expected improvement or worsening of the first patient due to the disease is relative to an initiation date of a therapy.

16. The system of claim 1, wherein the at least one processor is further programmed to
generate an estimate indicative of how much a tumor in the first patient is predicted to shrink or grow over a predetermined time period after an initiation date of a therapy.

17. The system of claim 1, wherein:
the subset of medical records in the plurality of medical records comprises a first subset of medical records; and
the machine learning model is associated with a predicted performance measure, the predicted performance measure being generated based at least in part on at least one performance status score for a third patient associated with a second subset of medical records in the plurality of medical records by inputting a third feature extracted from the second subset of medical records into the machine learning model, wherein the second subset of medical records does not overlap with the first subset of medical records.

18. The system of claim 1, wherein each record in the plurality of medical records lacks a structured ECOG score for a patient associated with said each record.

19. The system of claim 1, wherein extracting at least one of the first extracted feature or the second extracted feature comprises applying a natural language processing algorithm.

20. The system of claim 19, wherein the natural language processing algorithm comprises at least one of a logistic regression, a neural network, a random forest algorithm, or a cox proportional hazards regression algorithm.

21. The system of claim 19, wherein the natural language processing algorithm applies a lasso regression analysis.

22. A method for predicting a performance status of a first patient, the method comprising:
accessing a database storing a plurality of medical records, wherein each medical record in the plurality of medical records comprises at least one of structured or unstructured information;
extracting a first feature from a subset of medical records in the plurality of medical records;
training a machine learning model based on the first extracted feature, wherein training the machine learning model comprises correlating the first extracted feature with at least one known result for a second patient associated with the subset of medical records;
extracting a second feature from at least one medical record in the plurality of medical records, wherein the at least one medical record is associated with the first patient and lacks a structured ECOG score for the first patient;
inputting the second feature into a trained machine learning model to generate an ECOG score for the first patient; and
generating, based at least in part on the generated ECOG score for the first patient, an output indicative of a suitability of the first patient for inclusion in a clinical trial.

23. The method of claim 22, wherein the machine learning model comprises at least one of a logistic regression model, a neural network, or a random forest model.

24. The method of claim 22, wherein the at least one medical record associated with the first patient includes structured information on at least one of a gender, a birth date, a race, a weight, a lab result, a vital sign, a diagnosis date, a visit date, a medication order, a diagnosis code, a procedure code, a drug code, a prior therapy, or a medication administration.

25. The method of claim 22, wherein the at least one medical record associated with the first patient includes unstructured information comprising at least one of text written by a health care provider, a radiology report, or a pathology report.

26. The method of claim 22, further comprising
presenting at least one of the generated ECOG score or the output indicative of the suitability of the first patient for inclusion in the clinical trial.

27. The method of claim 22, further comprising
generating a time estimate of expected improvement or worsening of the first patient due to a disease.

28. The method of claim 22, further comprising generating an estimate indicative of how much a tumor in the first patient is predicted to shrink or grow over a predetermined time period after an initiation date of a therapy.

29. The method of claim 22, further comprising generating a survivability score for the first patient.

30. A system for providing a performance status score for a patient, the system comprising:
   at least one processor programmed to:
      access a database storing a plurality of medical records for the patient, wherein the plurality of medical records comprises unstructured information;
      identify, based on the plurality of medical records, a line of treatment associated with the patient, wherein the plurality of medical records lacks a structured ECOG score for the patient associated with the line of treatment;
      query a subset of the unstructured information in the plurality of medical records using at least one keyword to retrieve at least one medical record in the plurality of medical records;
      extract an ECOG score for the patient associated with the line of treatment from unstructured information of the at least one retrieved medical record using at least one of a trained machine learning model or a natural language processing algorithm; and
      generate, based at least in part on the extracted ECOG score for the patient, an output indicative of a suitability of the patient for inclusion in a clinical trial.

31. The system of claim 30, wherein the queried subset of unstructured information comprises unstructured information generated within a predefined timeframe of a start date of the line of treatment.

* * * * *